United States Patent [19]

Cory

[11] Patent Number: 5,237,276
[45] Date of Patent: Aug. 17, 1993

[54] FEED MECHANISM AND METHOD THEREFOR

[75] Inventor: David G. Cory, Boston, Mass.

[73] Assignee: Bruker Instruments, Inc., Billerica, Mass.

[21] Appl. No.: 707,835

[22] Filed: May 30, 1991

Related U.S. Application Data

[63] Continuation-in-part of Ser. No. 663,709, Mar. 4, 1991, Pat. No. 5,200,702.

[51] Int. Cl.⁵ .................... G01R 33/30; G01R 33/46
[52] U.S. Cl. ................................ 324/321; 414/222; 414/224
[58] Field of Search ............. 324/321; 414/222–226, 414/332; 198/478.1

[56] References Cited

U.S. PATENT DOCUMENTS

| | | | |
|---|---|---|---|
| 4,091,323 | 5/1978 | Landis | 356/244 X |
| 4,518,264 | 5/1985 | Nohso | 422/65 X |
| 4,581,583 | 4/1986 | Van Vliet et al. | 324/321 |
| 4,654,592 | 3/1987 | Zens | 324/307 |
| 4,859,948 | 8/1989 | Kuster | 324/318 |
| 4,859,949 | 8/1989 | McKenna | 324/321 |
| 5,146,166 | 9/1992 | Bartuska | 324/321 |

FOREIGN PATENT DOCUMENTS

| | | |
|---|---|---|
| 0308654 | 3/1989 | European Pat. Off. |
| 62-63846 | 3/1987 | Japan |
| WO89/11646 | 11/1989 | PCT Int'l Appl. |

OTHER PUBLICATIONS

Bruker Instruments, Inc. *B BPS: A totally new concept in routine NMR automation* published by Jun. 1991; 6 pages.

Bruker Analytische Messtechnik GMBH 200-250-300 MHz NMR Spectrometer: *High-performance NMR Spectrometer for routine and research: AC P*; 12 pages, published by Jun. 1991.

Primary Examiner—Tom Noland
Attorney, Agent, or Firm—Cesari & McKenna

[57] ABSTRACT

Apparatus and method for sequential provision of a series of similarly configured objects to and from a proximal location such as a device for testing those objects. The objects are provided in a gravity-fed ramp to an open cylindrical container provided with a centrally pivoting rotatable drum. The drum is provided with an indentation configured to receive only one of the objects at a time. The drum is rotatably disposed in the open cylinder about a central pivot to rotatably move the indentation between a first position of the open cylinder at the foot of the walled ramp and a second position of the open cylinder. At the second position, the open cylinder is provided with a drop tube. At the second position, the received object drops into the drop tube and thence into a supply tube that communicates at one of its ends to gravity feed the object to the proximal location where the object is to be utilized. After the received object has been dropped at the second position into the drop tube, but before another such object can be received, the drum is rotated from the second position back to the first position wherein the indentation is at the foot of the ramp. The used object is ejected, by an appropriate force, from the proximal location back into the supply tube and thence to another container for disposed or used objects.

9 Claims, 7 Drawing Sheets

FEED MECHANISM AND METHOD THEREFOR

CROSS-REFERENCE TO RELATED APPLICATION

This is a continuation-in-part of U.S. patent application Ser. No. 07/663,709, filed Mar. 4, 1991, now U.S. Pat. No. 5,200,702.

FIELD OF THE INVENTION

The present invention relates to apparatus and method for repeatedly inserting and removing a succession of objects into a utilization device, particularly where those objects are substantially identically configured.

BACKGROUND OF THE INVENTION

In the field of automated measuring and testing equipment, one problem that must be addressed is the provision of test samples to, and removal of tested samples from, such equipment. A sample is inserted in the tester, which then automatically performs various tests, and the sample is then removed after testing and replaced with another sample. Sample changing can be done by hand. However, manual changing is slow, can result in contamination of the samples and requires the presence of an operator which partially defeats the purpose of automating the test equipment.

Accordingly, in the field of materials testing, it has been a general practice to employ automated devices for acquisition of a sample to be tested, transport of that sample to a testing apparatus, retrieval of the tested sample from the testing apparatus, and finally return of the sample whence it came or else provision of the tested sample to appropriate disposal. Often, such devices, particularly owing to their automatic nature, are designed or adapted to engage, transport and release samples of a predetermined size.

One example of a such a prior art automated testing device which handles predetermined size samples is a nuclear magnetic resonance (NMR) spectrometer, which includes a magnet chamber and a cylinder. Samples of material to be tested by the NMR spectrometer must be conveyed into the interior of the magnet chamber and, to that end, a sample is dropped into the cylinder and falls therethrough into the magnet chamber. After testing, the sample is ejected from the magnet chamber by any of various mechanisms.

An illustrative example of a magnet chamber 113 and a sample changer 117 for such an NMR spectrometer is shown in FIG. 8. Such a device is typical of NMR spectrometers available from Bruker Instruments, Inc., Billerica, Mass. Magnet chamber 113 is provided with a cylinder 115. Material samples are tested in magnet chamber 113 and such samples are inserted in and removed from chamber 113 via cylinder 115.

Magnet chamber 113 can be used for testing samples of both solid and liquid materials. Liquid samples are contained in sample holders made of glass which are easily broken. Consequently, it is necessary to handle the sample containers firmly but gently. Liquid sample holders are illustratively handled by material handling apparatus 117 which includes a vertical cylinder 119 and piston 121 mounted on a rotatable arm 123. The lower end of piston 121 is provided with a pneumatically-controlled pincher 137 for picking up and carrying a liquid sample holder. Arm 123 is rotatably supported on motorized pole 125 by upper and lower fixture rings 127 and 129 each connected to arm 123, and by resting ring 131 on which lower fixture ring 129 rests. Pole 125 is also provided with a pipe or tube 133 which supports magazine belt 135. Magazine belt 135 is configured to hold a plurality of liquid samples, and is rotated with rotation of pipe 133 so that different samples can be presented at different times to pincher 137. Cabinet 139 provides controls for movement of pipe 133 and pole 125. Pincher 137 with cylinder 119 and piston 121 can be moved horizontally or radially along arm 123, and may be moved azimuthally by swinging of arm 123 by rotation of pole 125 caused by cabinet 139. Pincher 137 is connected to the lower end of piston 121, and can be controlled to open and close about a liquid sample at belt 135 and cylinder 115. Cylinder 119, piston 121, arm 123 and pole 125 can thereby move pincher 137 between belt 135 and cylinder 115. Once the sample holders are inserted into cylinder 115, they are conveyed pneumatically to the interior of magnet chamber 113 and subsequently pneumatically ejected from chamber 113 after testing is completed.

The material handling apparatus 117 functions well to handle the delicate liquid sample holders. Magnet chamber 113 can also be modified to handle solid sample holders to enable the spectrometer to automatically test such samples. Typical solid sample holders are considerably smaller than liquid sample holders and are much more rugged. In particular, as shown in FIGS. 9 and 10, solid samples are typically disposed in a holder 151 which includes cap 147 and hollow ceramic tube 149. In one version of holder 151, cap 147 is tightly press-fitted on tube 149 whose opposite end is closed. Once inside magnet chamber 113 of the spectrometer, in accordance with well-known NMR spectroscopy techniques, holder 151 is rapidly rotated by compressed air, and for this reason is called a "rotor".

Apparatus 117 is obviously complicated and expensive and well-suited to handling fragile holders such as the liquid sample holders. Since the ceramic solid sample rotors are much more rugged than the glass liquid sample holders, it is no longer necessary to use the aforementioned complicated pincher mechanism to delicately transport the rotors between a moving supply belt or other source of supply and the spectrometer, if that were possible.

Furthermore, difficulty has been encountered with regard to the above-mentioned modification of magnet chamber 113 to handle rotors. Inside magnet chamber 113, the toothed or ratcheted edges of cap 147 are engaged by compressed air to rotate the sample in a technique known in the art as "magic angle" spinning. This rapid rotation, for proper testing, must occur at a particular angle with respect to the magnet chamber 113. This "magic angle" is 54.7° with respect to the direction of the magnetic field of magnet chamber 113. In order to place a rotor 151 in the proper position at the proper angle within magnet chamber 113 for testing, it has been found necessary to require the rotor, when dropped into magnet chamber 113, to follow a winding path to the location within the magnet chamber where it will be tested. One example of such a path is shown in International Patent Application WO 89/11646 published Nov. 30, 1989 for "NMR-Spectrometer With Sample Exchanger" in the single figure thereof, which published application is hereby incorporated by reference herein. Typically, a blast of compressed air is used to insert the rotor into, and a separate blast of compressed air is used to eject the rotor from, that location. Particularly because of the winding path which the rotor must follow to and from the location within magnet chamber where it is to be tested, difficulty has been encountered in properly seating the rotor 147 at that location so that it can be tested.

Accordingly, there is a need for a sample changer providing rapid, easy changing of samples of solid material to and from a device that tests such samples. The present invention fulfills that need.

SUMMARY OF THE INVENTION

Accordingly, it is the general purpose of the present invention to provide apparatus and method for repeated exchanging of similarly configured objects at a predetermined location.

Other objects of the present invention are to provide apparatus and method for sequentially inserting and removing solid samples to and from a material tester.

Further objects of the present invention are to provide a sample changer for an NMR spectrometer which treats rotors for solid samples as if they are robust, not fragile, devices.

A still further object of the present invention is to provide method and apparatus for correcting any improper seating of a rotor for a solid sample within the magnet chamber of an NMR spectrometer.

Briefly, these and other objects of the present invention are accomplished by an apparatus wherein a plurality of similarly configured objects are provided in a gravity-fed stack to a changer that includes a container, a holder slidably disposed in that container, and a mover for transporting the holder between two positions within the container. The mover can be disposed within or outside of the container, and can be a two-way pneumatic valve, a driven rod having detents for defining the two positions, a motor, a solenoid or any other suitable device. In one of the two positions, the holder is disposed under the stack of objects being fed to receive one of those objects. In the other position, the holder is positioned to gravity feed the object to a location where it is to be utilized. The holder can be configured with a single-location, or with two parallel locations, each of which can receive one object. For a single-location holder, the second position is also utilized to permit ejection of the used object, by an appropriate force, from the using location. For a two-location holder, the first position is utilized for the purpose of ejection, so that receipt of another one of the objects can take place while or even before the fed object is so ejected.

Alternatively, the present invention can be accomplished by an apparatus wherein a plurality of similarly configured objects are provided in a gravity-fed slide or ramp to a rotatable drum or disk disposed in an open cylindrical container. The drum is provided with an unfloored open niche or indentation configured to receive a single such object. The drum is then rotated about its axis, such as via a central pivot, such that the niche and the object received therein are transported by the drum from a first position at the foot of the slide to a different location in the container that is provided with a drop tube. The drop tube angles downwardly and is connected to the side of a supply tube in a branching fashion. The supply tube empties at one end into the location or device utilizing those objects, such as a magnet chamber of an NMR spectrometer. The supply tube is connected at its other end to a container for the used objects. The objects fall from the niche of the drum in the second position, down the drop tube into the supply tube, and thence into the using device. After use, the object is ejected from the using device through the supply tube to the container at the other end of the supply tube. A presence sensor such as a light sensor can be provided to detect when the fed object passes or is about to pass from the supply tube into the using device. A pin or similar blocking device can be utilized to prevent ejection of the object until after its use or some other event occurs, such as a determination that the object cannot be properly positioned in the using device.

The present invention is furthermore accomplished by shifting such objects mechanically into and out of an air stream or other fluid stream. Such objects are furthermore accomplished in the present invention by treating such objects as robust as opposed to fragile devices, by collecting such objects by permitting one such object to impact another.

The present invention is furthermore accomplished by providing a pin or similar blocking device for blocking the path to be followed by the fed object after it has been provided to the location or device utilizing such object. Normally, the blocking device would not be positioned to block that path. Sensing of improper seating of the fed object at such location or device can be utilized to cause such blocking device to block that path. With the path so blocked, the fed object can then be ejected from the using location or device, caused to impact the blocking device, and then permitted to fall back into the location or device to attempt proper reseating. After a predetermined number of such attempts, indicating futility of further such attempts, the blocking device can be caused to withdraw to its normal position with the travel path left clear, so that the fed object can be ejected and any subsequent such object can be inserted in substitution therefore.

Other objects, advantages and novel features of the invention will become apparent from the following detailed description of the invention when considered in conjunction with the accompanying drawings.

DESCRIPTION OF THE PREFERRED EMBODIMENTS

Figure 1:
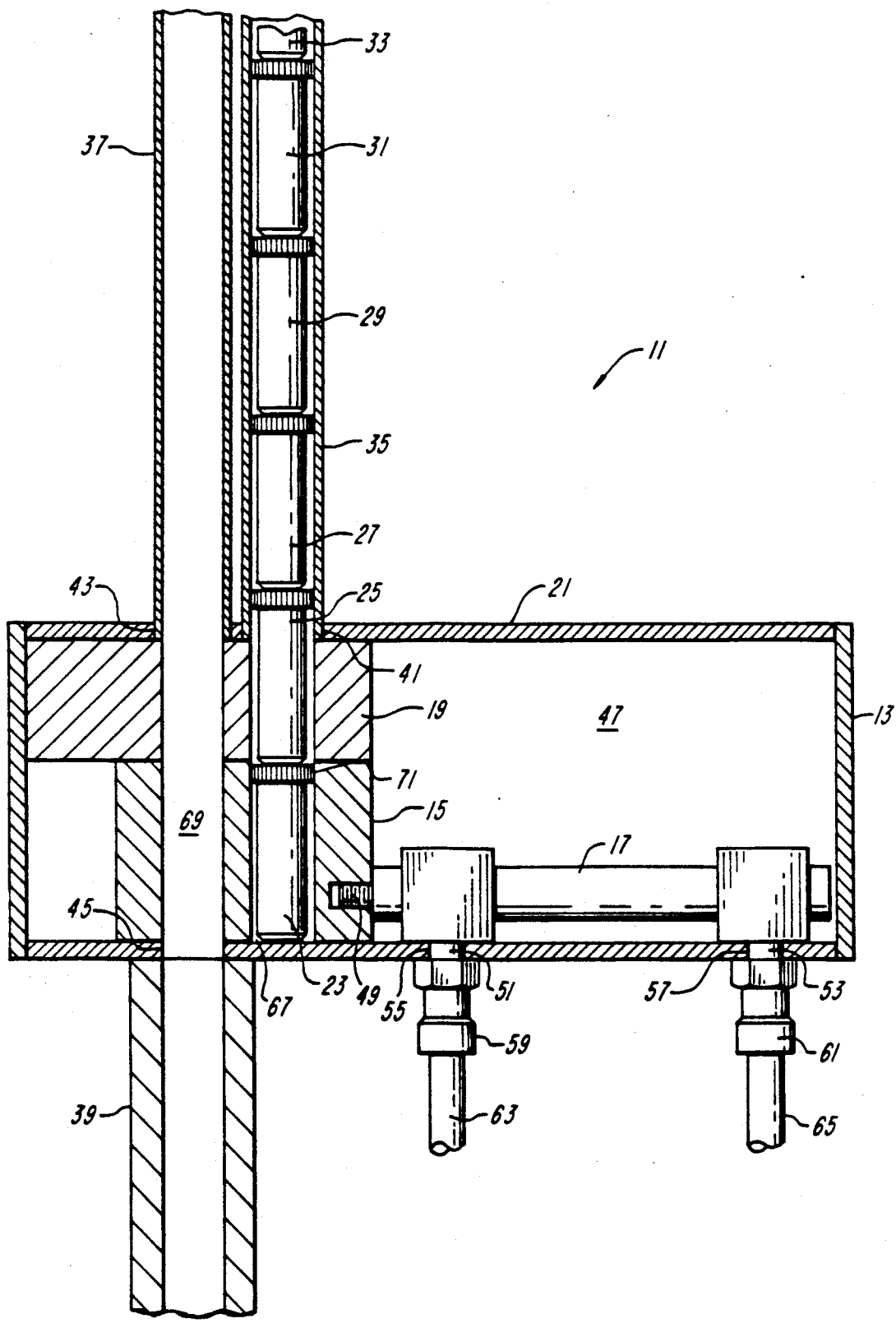
FIG. 1 shows a sectional view of one embodiment of a sample changer according to the present invention and shown in one operating position.
Figure 8:
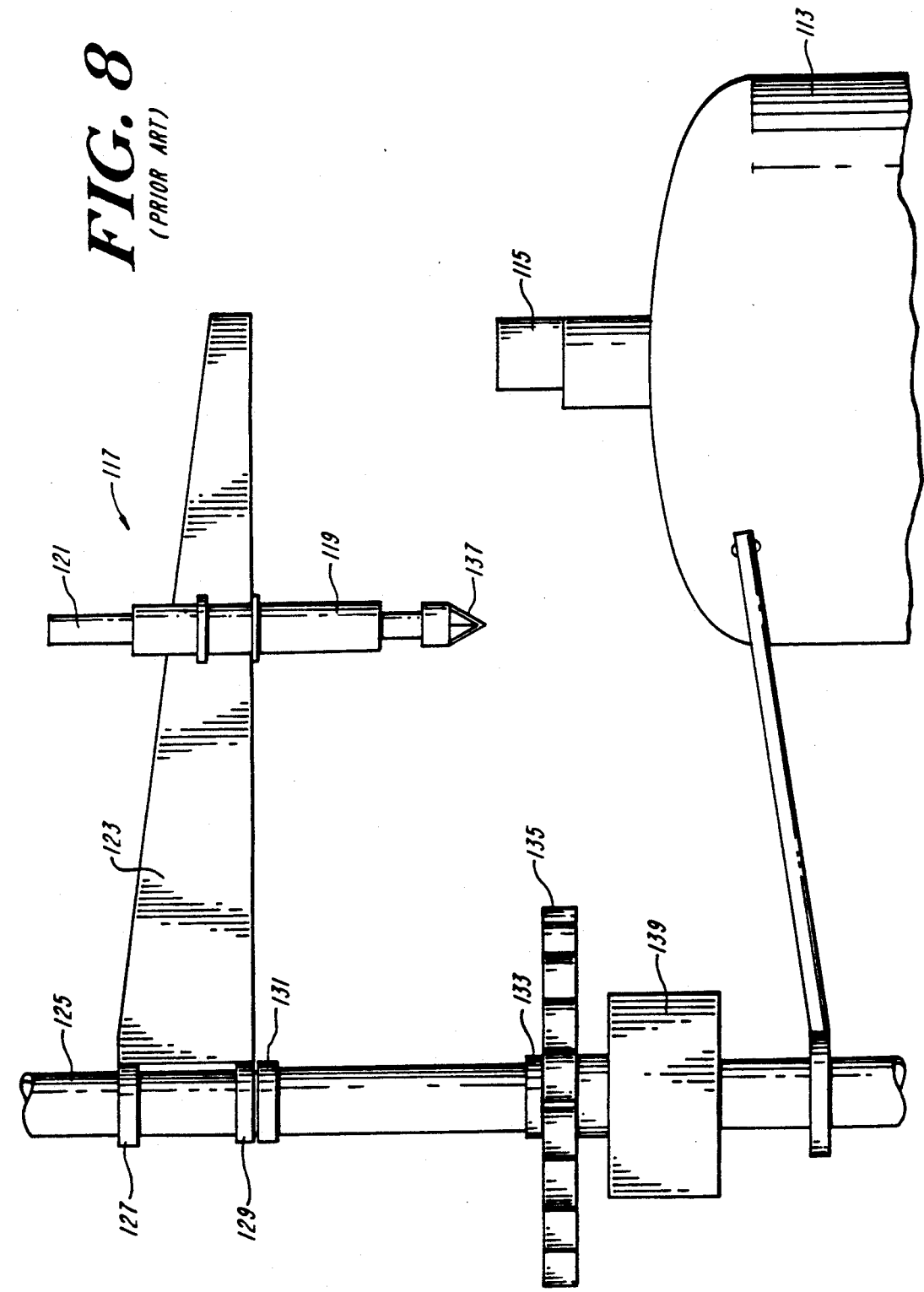
FIG. 8 shows a side elevation of a prior art material handling and testing apparatus.
Figure 9:
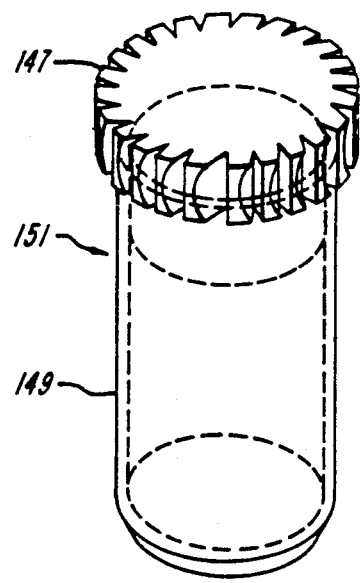
FIG. 9 illustrates a prior art holder for material samples to be tested, for which the apparatus of FIGS. 1-7 and 11-12 is particularly well suited.

Referring now to the drawings, wherein like reference characters designate like or corresponding parts throughout the several views, there is shown in FIG. 1 a sample changer 11 including a case 13 which is suitable for use with the NMR spectrometer described above in connection with FIGS. 8 and 9. Disposed within case 13 are holder 15 slidably disposed in the case, two-way pneumatic drive 17 connected to and driving the holder, and spacing block 19 spacing the upper wall 21 of the case away from holder 15 so that the next lowest sample rotor 25 of sample rotors 23-33 can enter the case. However, inclusion of block 19 in the apparatus of FIG. 1 is not absolutely necessary; instead, upper wall 21 could be disposed just above and in slidable contact with holder 15.

Figure 2:
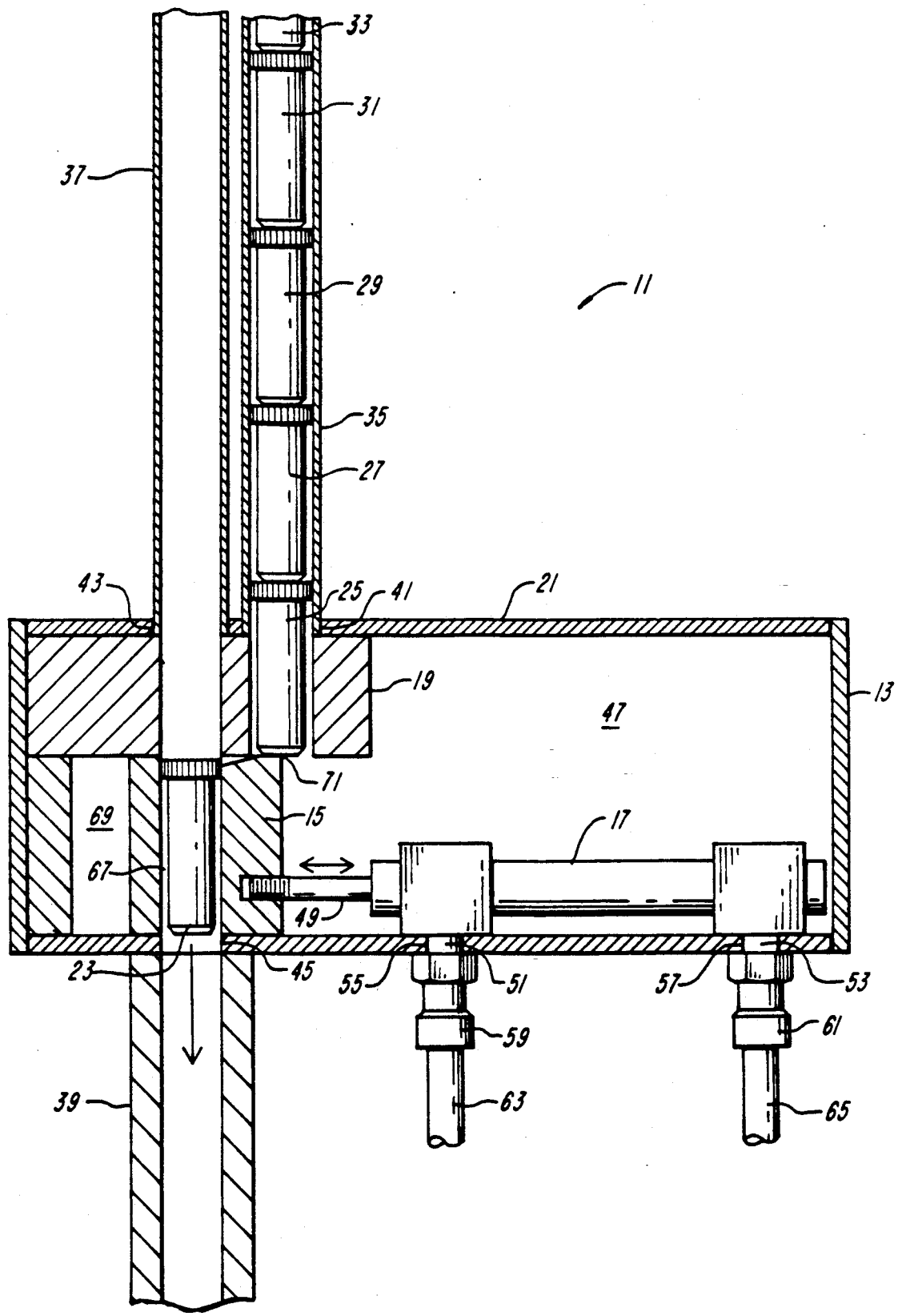
FIG. 2 is a sectional view of the apparatus of FIG. 1 shown in a second position of operation.

Sample changer 11 further includes feed tube 35, eject tube 37 and insertion tube 39, each engaging or otherwise connected to a corresponding opening 41, 43 or 45 of case 13. Holder 15 is slidably disposed in interior chamber 47 of case 13, and is moved between a first position (shown in FIG. 1) and a second position (shown in FIG. 2) by drive 17. Drive 17 is typically provided with a piston 49, and is provided with two input ports 51 and 53 for receipt of compressed air or other fluid, each for moving that piston in one of the two directions shown in FIG. 2. For example, application of compressed air at port 53 would result in sideways movement of holder 15 from the first position of FIG. 1 to the second position of FIG. 2. Also, input of compressed air at port 51 would move holder 15 to the right as shown in FIGS. 1 and 2, for example, from the second position of FIG. 2 to the first position of FIG. 1. Case 13 is provided with respective openings 55 and 57 for ports 51 and 53. A respective connector 59 and 61 connects respective ports 51 and 53 to respective pneumatic lines 63 and 65. Case 13, holder 15 and block 19 can, for example, each be of aluminum. Tubes 35, 37 and 39 can, for example, each be of brass.

Figure 3:
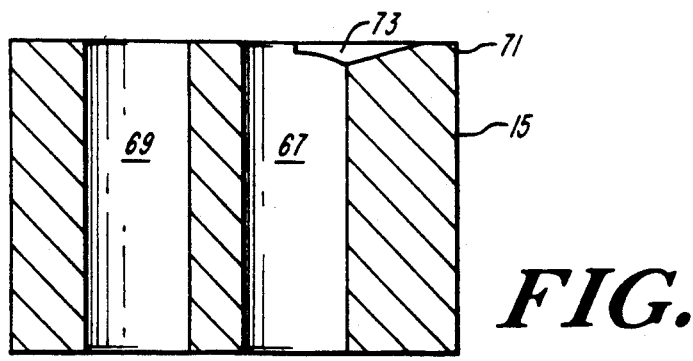
FIG. 3 is a sectional view of a portion of the apparatus of FIGS. 1 and 2 more clearly showing details thereof.
Figure 4:
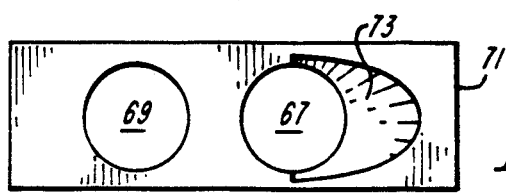
FIG. 4 is a top view of the portion of FIG. 3.

Operation of the embodiment of FIGS. 1 and 2 will now be described. Rotors 23-33, each holding a sample of solid material to be tested, are inserted into and stacked in feed tube 35. If holder 15 is in the first position of FIG. 1, then the lowest rotor 23 will enter compartment 67 of holder 15. Otherwise, the lowest rotor would enter block 19, but would be held above holder 15 by its edge 71 until drive 17 moves the holder to the first position. After the lowest or bottom rotor 23 has entered compartment 67 of holder 15, and when the spectrometer or other device is ready to receive a sample for testing, compressed air from line 65 closes drive 17 to urge the holder leftwards to the second position of FIG. 2. In the position of FIG. 2, rotor 23 would simply drop via opening 45 and insertion tube 39 into magnet chamber 113. Preferably, compressed air from line 63 would close drive 17 to move holder 15 rightwards to the first position of FIG. 1 so that the next rotor 25 can enter compartment 67. In order to avoid any problems with a rotor catching on the upper entrance to compartment 67 and thereby interfering with proper movement of holder 15 and proper entry of the rotor therein, rotor 15 is furthermore provided with bevelled or sloped indentation 73, which is more clearly shown in FIGS. 3 and 4, and slopes or inclines into compartment 67. When the spectrometer has finished testing rotor 23, it ejects that rotor from magnet chamber 113 using a blast of compressed air. That blast of ejection air causes the tested rotor to pass through insertion tube 39, compartment 69 and eject tube 37. For this reason, eject tube 37 and insertion tube 39 are aligned.

The holder or slider 15 has two holes 67 and 69 through it, which are the same diameter as tubes 35, 37 and 39. In its rest or first position, these two holes are respectively positioned directly below the feed 29 and ejection 37 tubes. Feed tube 35, as discussed above, is filled with rotors, stacked one on top of the other. Due to gravity, the bottom rotor 23 will fall into hole 67 and slider 15. In order to insert a rotor into magnet chamber 111, pneumatic pressure is applied to piston 49, causing the piston to push the slider away from it. This positions the rotor, which is in slider 15, over insert tube 39. Due to gravity, the rotor falls into the spectrometer. In order to eject the tested rotor, pneumatic pressure is applied to the other side of piston 49, causing it to return slider 15 to its rest position. A second hole 69 in slider 15 permits the tested rotor, under pneumatic pressure from the spectrometer, to pass from insert tube 39 through hole 69 to eject tube 37 and out of changer 11. At the same time, another rotor can fall from feed tube 35 into slider 15. There are a number of possibilities for catching the ejected rotor. A simple basket of netting may be attached to eject tube 37, or a more elaborate structure may be devised to drop the tested rotor into a catch basin or collection tube.

A second embodiment of the present invention is shown in FIGS. 5A-5D in various positions and various stages of operation. This sample changer 75 is primarily differentiated from sample changer 11 of FIGS. 1-4 in that it includes a holder or slider 77 having only one compartment or hole 79 for receiving rotors 23-27. Like sample changer 11, sample changer 75 includes a case 81 with an interior chamber 83, a spacing block 85, a feed tube 87, an eject tube 89 and an insertion tube 91. Although no drive such as drive 17 of FIGS. 1 and 2 is shown in FIGS. 5A-5D for simplicity, it will be appreciated that some such drive is needed to move slider 77 between its first position of FIGS. 5A and 5D and its second position of FIGS. 5B and 5C. As with insertion tube 39 of FIGS. 1 and 2, insertion tube 91 of FIGS. 5A-5D is connected to, or is disposed at least partially within, a spectrometer or other testing device such as within magnet chamber 113 of an NMR spectrometer.

Figure 5A:
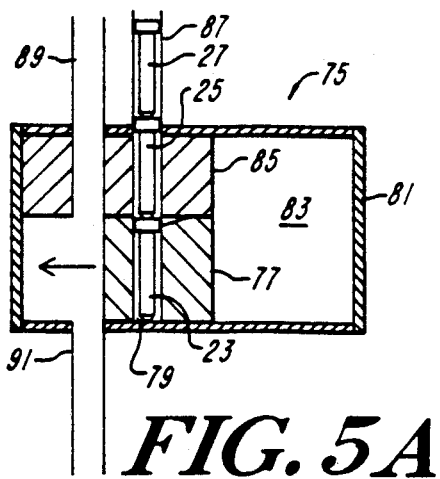
FIG. 5A is a sectional view of another embodiment of a sample changer according to the present invention shown in a first operating position during a first stage of operation.
Figure 5B:
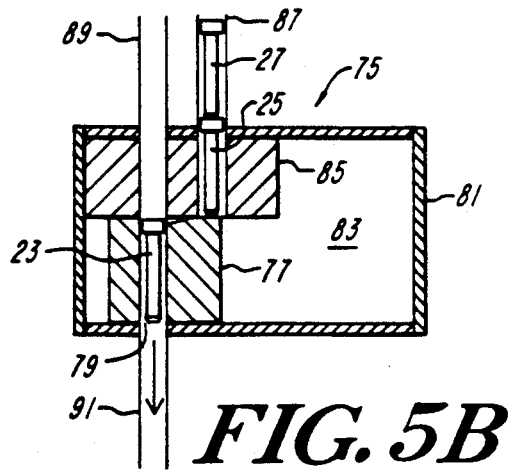
FIG. 5B is a like sectional view of the apparatus of FIG. 5A shown in a second operating position during a second stage of operation.
Figure 5C:
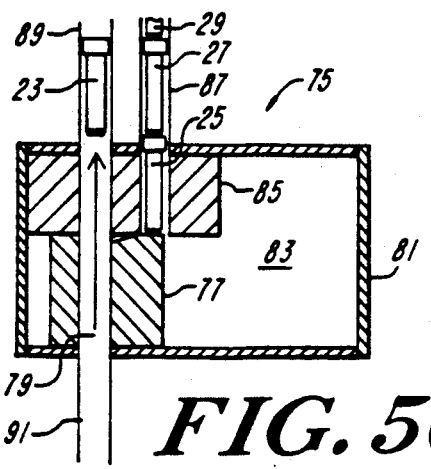
FIG. 5C is a like sectional view of the apparatus of FIG. 5A shown in the second operating position of FIG. 5B but in a third stage of operation.
Figure 5D:
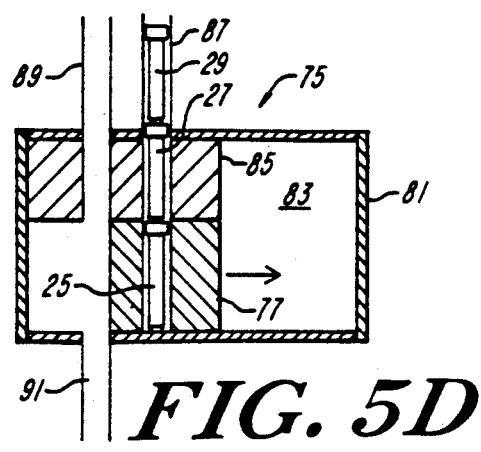
FIG. 5D is a like sectional view of the apparatus of FIG. 5A shown in the first operating position but during a fourth stage of operation which leads to the first stage of operation of FIG. 5A.

Operation of the embodiment of FIGS. 5A-5D will now be described. In the following description of operation, slider 77 is being moved by a suitable mover or driver (not shown) controlled by a suitable pair of input ports having feed lines connected thereto (also not shown). Operation is preferably initiated in the position of FIG. 5A. Again, a plurality of rotors 23, 25, 27, etc. is inserted into feed tube 87 in a stack with the bottom rotor 23 entering bore 79 of slider 77. Slider 77 is then moved leftwards into its second position of FIG. 5B. In the position of FIG. 5B, gravity or other suitable force causes rotor 23 to drop through insertion tube 39 into the testing device for testing. As shown in FIG. 5C, slider 77 remains in its second position during ejection of rotor 23 from magnet chamber 113 or other testing device. As described above, after the NMR spectrometer has finished testing a rotor in magnet chamber 113, it ejects that rotor with a blast of compressed air. Tested rotor 23 when ejected thereby is impelled through insertion tube 91, bore 79 and eject tube 89. Thereafter, as shown in FIG. 5D, slider 77 is moved rightward into its first position so that the next rotor 25 can drop into bore 79. The cycle of FIGS. 5A-5D is then repeated, this time with rotor 25 being tested.

Although a pneumatic drive is shown as drive 17 in FIGS. 1 and 2, it should be understood that any sort of drive can be utilized with the present invention. For example, drive 17 could be replaced with a piston or a rod having the appropriate detents to limit its movement between what would correspond to the first and second positions of the slider 15 or 77. Alternatively, a solenoid, a hydraulic actuator, a motor, or any other suitable moving or impelling device could be utilized to move slider 15 or 77 between its first or second positions. However, a pneumatic drive is preferred for this purpose, to take advantage of the compressed air used for insertion and ejection of rotors in magnet chamber 113. For example, for the embodiment of FIGS. 1-4, the compressed air used for insertion of a rotor in magnet chamber 113 could also be provided to line 63, and the compressed air used for ejection of a rotor from the spectrometer could also be provided to line 65. In this way, positioning and movement of slider 15 could be coordinated with operation of the NMR spectrometer, resulting in fully automatic operation. For example, a stack of rotors could be loaded into feed tube 27, the NMR spectrometer could then be turned on, and the apparatus left to operate over the weekend with no human attendant required.

Figure 6:
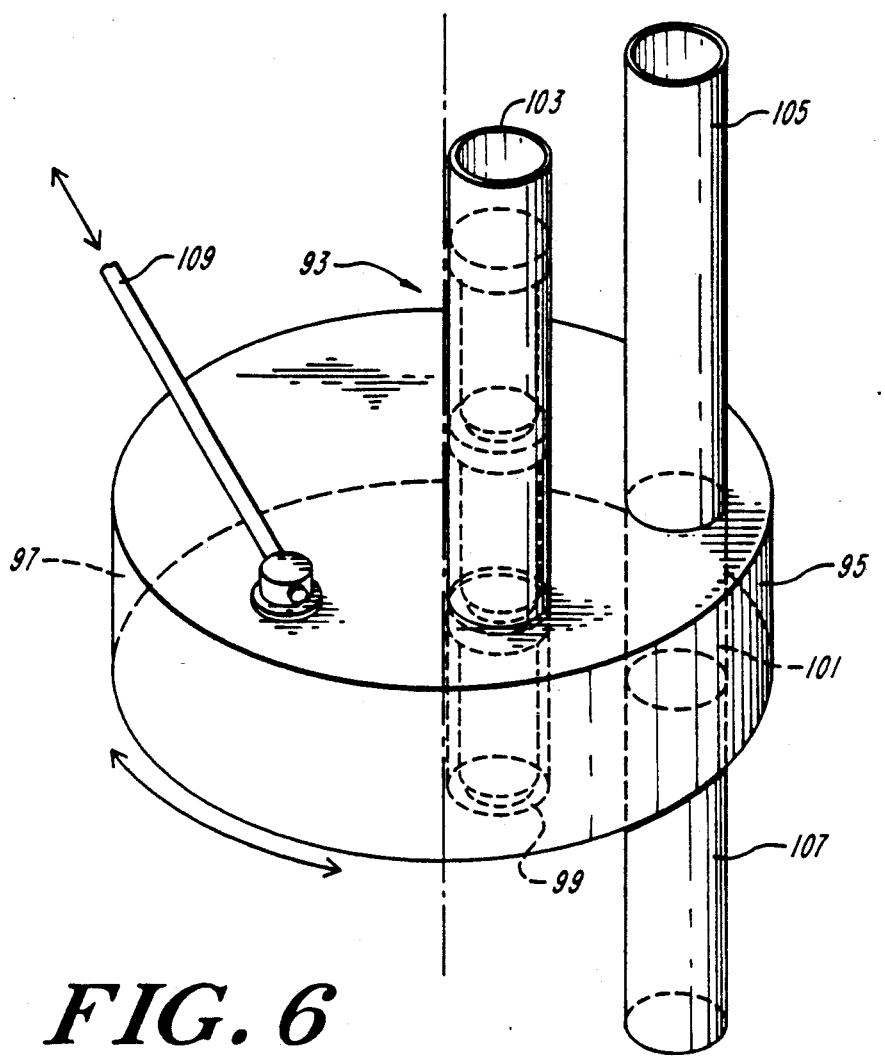
FIG. 6 is an orthogonal view of a third embodiment of a sample changer according to the present invention with certain portions hidden in that view shown with broken lines.

A third embodiment of the present invention is shown in FIG. 6. In this third embodiment, sample changer 93 includes a cylindrical or drum-shaped case 95 containing a disk 97 provided with bores 99 and 101. Sample changer 93 further includes feed tube 103, eject tube 105, and insertion tube 107. Disk 97 is pivotably rotated within cylinder 95 between a first position as shown in FIG. 6 with bore 99 being disposed below feed tube 103, and a second position counterclockwise from the first position wherein bore 99 is disposed in alignment with eject tube 105 and insertion tube 107. Such movement is accomplished by suitable drive means (not shown), but which can be controlled via an electric or other line 109, a pair of pneumatic lines (not shown), or other suitable means. Otherwise, operation of the embodiment of FIG. 6 is similar to that of the embodiment of FIGS. 1-4.

Figure 12:
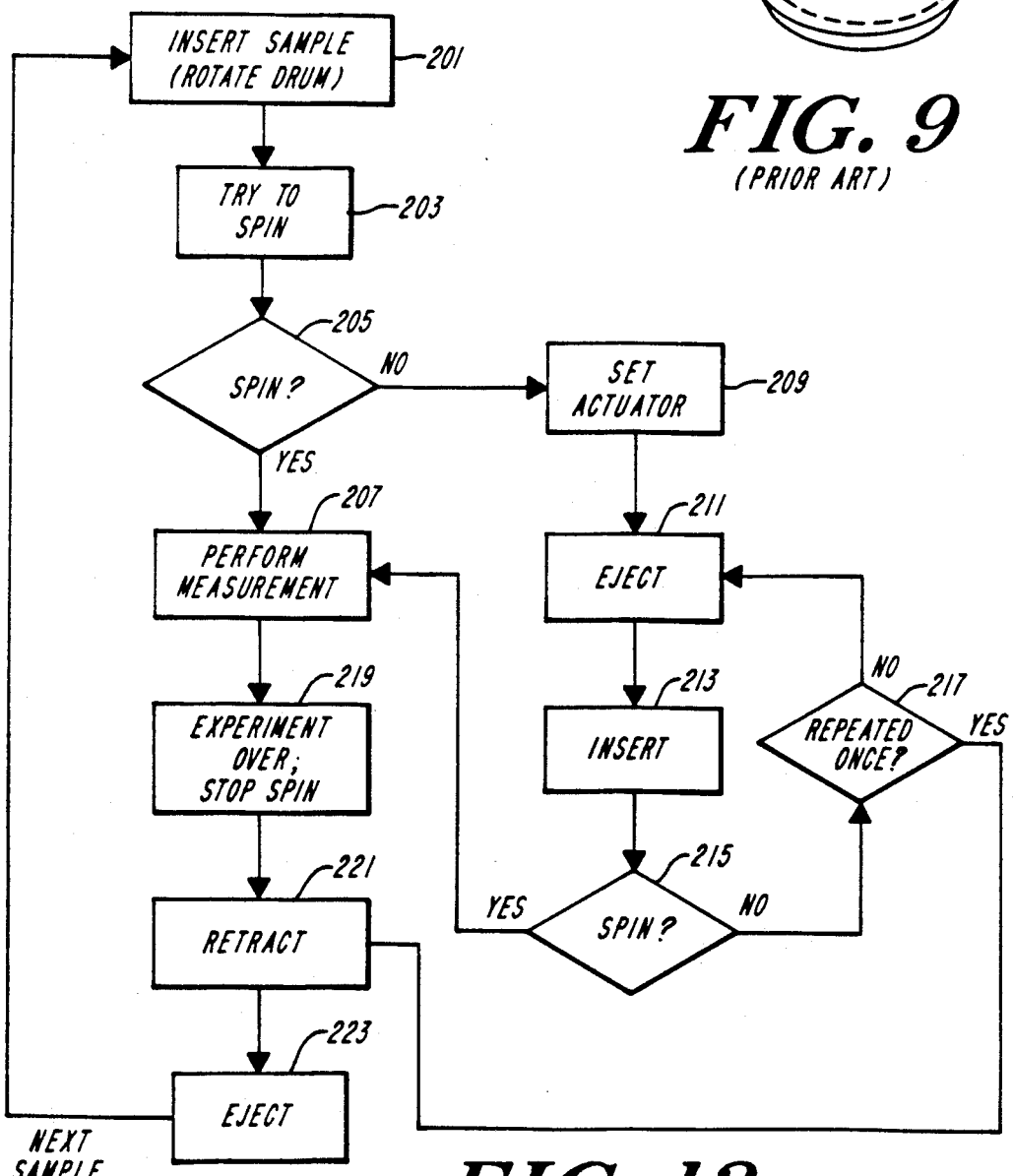
FIG. 12 is a flowchart illustrating the sequence of operation of the sample changer of FIG. 11.
Figure 11:
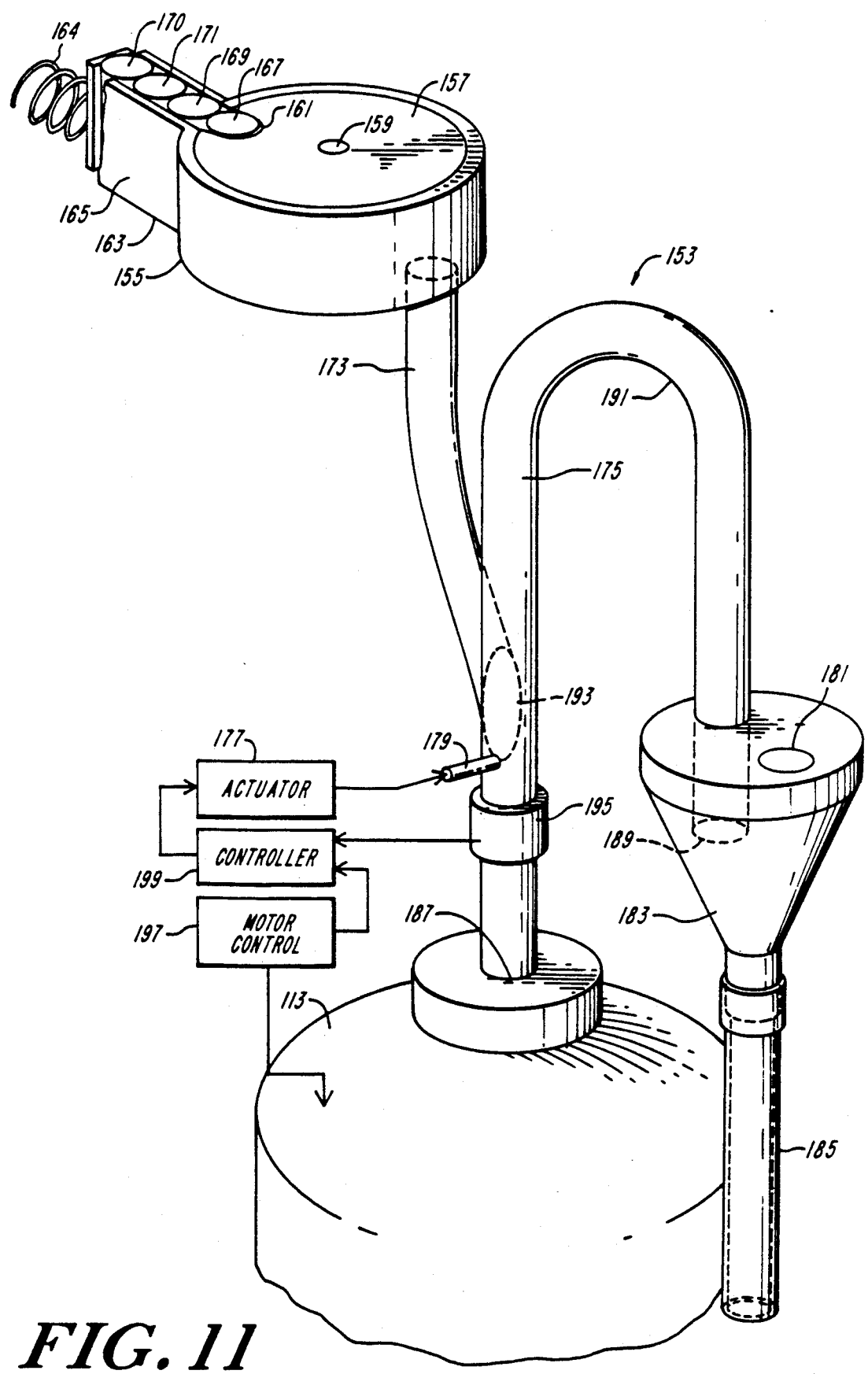
FIG. 11 illustrates a fourth embodiment of a sample changer according to the present invention.

Alternatively, as shown in FIG. 11, the rotors can be provided in a gravity-fed walled 165 ramp 163 to an open cylindrical container 155 provided with a centrally pivoting rotatable drum 157. The drum 157 is provided with an indentation 161 configured to receive only one of the rotors 167, 169, 171, etc. at a time. Drum 157 is pivotably 159 rotated within cylinder 155 between a first position as shown in FIG. 11 with indentation 161 being disposed below feed ramp 163, and a (preferably) substantially antipodal second position wherein indentation 161 is disposed in alignment with feeder tube 173. Such movement is accomplished by suitable drive means (not shown), which can be controlled via an electric or other line, one or more pneumatic lines, or other suitable means (not shown). Such rotation of drum 157 from the first to the second positions and vice versa is preferably all in the same direction, i.e. either all clockwise or else all counterclockwise. The drum 157 is rotatably disposed in the open cylinder 155 about a central pivot 159 to rotatably move the indentation 161 between a first position of the open cylinder 155 at the foot of the walled ramp 163 and a second position of the open cylinder 155. At the second position, the open cylinder 155 is provided with a drop tube 173. At the second position, the received rotor drops from indentation 161 into the drop tube 173 and thence into a supply tube 175. Supply tube 175 communicates at one of its ends to gravity feed the rotor to the magnet chamber 113 where the rotor is to be tested. After the received rotor has been dropped at the second position into the drop tube 173, but before another such rotor can be received by the indentation 161, the drum 157 is rotated from the second position back to the first position, so that the indention 161 is again at the foot of the ramp 163. The used rotor is ejected, by an appropriate force, from the magnet chamber 113 back into the supply tube 175 and thence via funnel or cone 183 to a container 185 or other location for disposed or used rotors. The sample tube 175 preferably has a lower end 187 connected to the magnet chamber 113 and an upper end 189 connected to the disposal container 185, with a curved portion 191 therebetween. Drop tube 173 preferably slopes downwardly and diagonally into the supply tube 175 at joint 193 below that bend 191, so that unused rotors cannot be provided to the disposal container 185, and ejected used rotors cannot be returned to the drop tube 173 and the cylinder 155. A selective detent 179 such as a sliding pin controlled by actuator 177 can be provided to temporarily block off the supply tube 175 below the entry 193 of the drop tube 173. Detent 179 thereby permits improperly seated objects to be ejected against the detent and returned to the magnet chamber 113 for reseating. Detent 179 can also be used, if desired, to prevent ejection of a rotor from magnet chamber 113 until after it has been tested. Pin 179 is withdrawn from tube 175 to permit ejection from magnet chamber 113 of tested rotors, and to permit ejection of unused rotors which cannot be properly seated after a predetermined number (preferably two) of attempts. At or near the magnet chamber 113, the supply tube 175 can be provided with a presence or proximity sensor 195 such as a light sensor for detecting passage of each such object. Sensor 195 is used to control operation of the magnet chamber 113 and its pneumatics, as well as to control operation of the drum 157 and the pin 179. Actuator 177 is controlled by controller 199, which receives inputs from sensor 195 and from magnet chamber 113 motor control 197. The preferred sequence of operation of sample changer 153 is shown in FIG. 12.

A fourth embodiment of the present invention is shown in FIG. 11. In this fourth embodiment, sample changer 153 includes a cylindrical or drum-shaped case or container 155 containing a solid or hollow disk or cylinder 157 rotatably disposed therein about a central pivot 159. Pivot 159 can, for example, be an axial pivot. Cylinder 157 is provided with an open niche or indentation 161. Niche 161 is sized and configured to receive one rotor 151, but no more than one such rotor, at a time. Niche 161 is unfloored. Rotors 167, 169, 171 are provided to case 155 via an inclined slide or ramp 163 having its lower end opening into case 155. Alternatively, rotors 167, 169, 171 can be sequentially provided to niche 161 via a vertical stack such as is shown in FIGS. 1, 2, 5A-5D, 6 and 7. Slide 163 is preferably provided with side walls 165, to prevent rotors 167, 169, 171 from falling off. The rotors 167, 169, 171 shown in FIG. 11 are urged down slide 163 towards niche 161 under spring tension from spring unit 164 which bears upon rotor 170 from the rear. Alternatively, gravity and the weight of the upper rotor(s) (not shown) could be used for this purpose. Cylinder 157 transfers each such rotor in turn from a first position at the foot of slide 163, to feeder tube 173 disposed in the bottom of case 155 at a second position preferably disposed 180° from the first position. Cylinder 157 need not be the same height as rotors 167, 169, 171, etc.

Rotors 167, 169, 171 to be tested are lined up in slide or holder 163 which delivers them one at a time to cylinder 157, which corresponds to a simple gear. Niche 161 of cylinder 157 accepts one such rotor at a time and makes a complete revolution at a signal from magnet chamber 113. Halfway through that revolution, the received rotor is delivered to the sample insert tube 173 via a hole in the case or gear housing 155. Feeder tube 173 is connected to the insert tube 175. Insert air for the magnet chamber 113 is turned on during this operation to seat the rotor correctly in the magnet chamber.

The rotor falls into magnet chamber 113 under gravity, and pneumatic pressure is used to insert and eject each rotor. As the rotor falls down insert tube 175 to magnet chamber 113, the rotor interrupts a light beam at sensor 195 while traveling through the sample insert tube 175. The signal resulting from this interruption of the light beam is used to indicate that rotor will soon be, or is, in the magnet chamber 113. If the inserted rotor becomes correctly seated in magnet chamber 113, the NMR spectrometer then spins and tests the sample in the rotor. If the rotor is not properly seated in the magnet chamber (i.e. it refuses to spin as described above), then an actuator 177 inserts a thin plastic rod or other movable detent 179 across sample insert tube 175. Actuator 177 can for example be a servo mechanism or a coil with magnet device. When the spin control unit of the NMR spectrometer tries to spin an inserted rotor in magnet chamber 113, it optically looks at the bottom of the rotor for a locator or presence dot 201, shown in FIG. 10. If that dot 201 is not seen, then actuator 177 is actuated by motor control 197 to insert pin 179 into insert tube 175. The rotor is then ejected by compressed air from magnet chamber 113 until it again interrupts the light path for sensor 195. Upon such interruption, the ejection air is turned off and the insert air is turned on in an attempt to seat the rotor.

Figure 10:
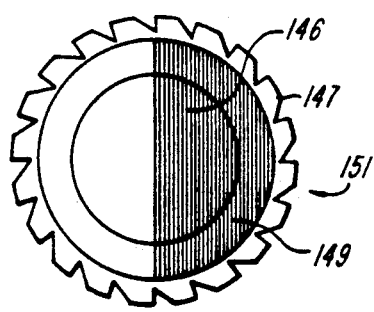
FIG. 10 is a bottom end view of the prior art sample holder of FIG. 9.

Sequence of operation of sample changer 153 of FIG. 10 is illustrated in FIG. 12. In step 201, drum 157 is rotated to insert a sample into magnet chamber 113. Insertion can be sensed by sensor 195. In step 203, motor control 197 attempts to spin the inserted rotor. At step 205, if the rotor does spin properly, then operation proceeds to step 207 where the inserted rotor is tested. If the rotor does not spin properly, however, then controller 199 sets actuator 177 to extend detent 179 into tube 175 above sensor 195. Controller 199 then causes motor control 197 to eject the rotor from magnet chamber 113 against detent 179, and to reinsert the rotor into the magnet chamber (step 213). Such ejection and reinsertion can be sensed by sensor 195. Another attempt is then made by motor control 197 to spin the rotor. Proper spinning of the rotor can be detected as described above. If the rotor still does not spin properly, then steps 211, 213 and 215 can be repeated for a fixed number of times, preferably once (step 217). If, after such repeated attempt(s), the rotor still does not spin properly, then motor control 197 via controller 199 causes actuator 177 to retract detent 179 (step 221), and the rotor is then ejected (step 223) into container 185 via bend 191 and funnel 183. Otherwise, the rotor is tested (step 207). When motor control 197 causes the rotor to stop spinning after testing of that rotor has been completed (step 219), thereafter the rotor is ejected (step 223) via tube bend 191 and funnel 183 into container 185 (step 223). Ejection of the rotor can be sensed by sensor 195. Operation then resumes with step 201, where a new sample is inserted into magnet chamber 113 via tubes 173 and 175. This sequence of operation is continued until all rotors then to be tested have been tested or discarded as unusable. Ordinarily, motor control 197 will have been programmed to test only a fixed number of rotors, corresponding to the number of rotors that have been inserted into ramp 163. Light sensor 195 can be used to verify some of these stages of operation.

After testing of the seated rotor is completed, or after a predetermined number of attempts fail to properly seat the rotor in magnet chamber 113 and actuator 177 withdraws pin 179 from blocking insert tube 175, the inserted rotor is then ejected from magnet chamber 113 into the insert tube. The "Y" or branching tubing arrangement that is formed at joint 193 by feeder tube 173 and insert tube 175 combines the insert and eject functions. A rapidly moving rotor ejected upwards should follow the straight path of insert tube 175 and should not try to move back up the feeder tube 173. The ejected rotor is impelled, by the ejection air from magnet chamber 113, up sample insert tube 175, through its curve 191, and down to enter covered cone or funnel 183. Cone 183 is preferably of soft plastic such as polypropylene, and is provided at its top cover with exhaust hole 181. The height and bend 191 of insert tube 175 slows down the ejected rotor, which then falls softly out of the bottom of funnel 183 and into a removable tube 185 which collects the used rotors one on top of another. Exhaust hole 181 permits release of air displaced in funnel 183 and tube 185 by the falling rotor. Alternatively, a bag (not shown) can be used at the bottom of funnel or cone 183 in lieu of tube 185. The feeding and ejection process can then be repeated with another rotor. In this manner, a set of rotors can be delivered to magnet chamber 113 one at a time, with provision for seating each such rotor correctly in the stator of the magnet chamber, and for collecting the ejected rotors after the completion of testing. When coupled with an automatic "magic angle" spinner controller such as motor control 197, sampler changer 153 provides completely automatic operation, and allows for a completely automated series of experiments or tests to be performed on a set of solid samples.

Funnel 183 can for example be of polypropylene. Funnel 183 preferably is made in one piece by blow molding, in a manner similar to that used for making plastic milk bottles. However, alternatively, funnel 183 can be made of two pieces, an open uncovered funnel and an open cylindrical cover or cap provided with exhaust hole 181, which are then pressure-fitted or glued together. Actuator 177 can for example be a servo motor. Actuator 177 can alternatively be a two-way pneumatic drive such as drive 17 of FIGS. 1 and 2. Sensor 195 is preferably located beneath selective detent 179 so that when a poorly or improperly seated rotor is ejected for reseating, presence of that rotor, as well as presence of any ejected used or rejected rotors, is thereby detected. Cylinder 157 can alternatively be provided with more than one niche or indentation, and its rotation would then preferably be in segments of less than 180° with a new rotor being provided thereto while a previously inserted rotor had not yet been ejected. Cylinder 157 can for example be a gear or a carousel.

Figure 7:
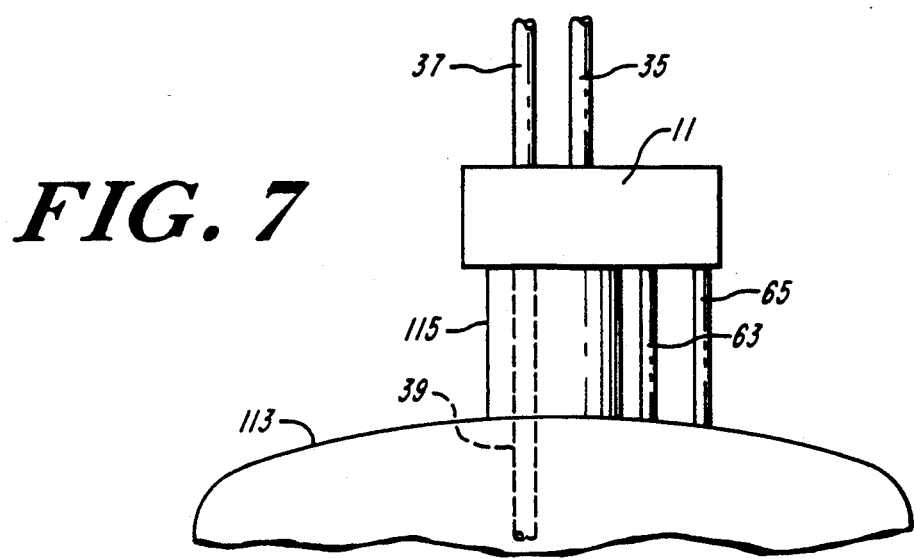
FIG. 7 shows a side elevation of a portion of a prior art NMR spectrometer showing a sample changer according to the present invention installed thereon.

As shown in FIG. 7, sample changer 11 (or for that matter, sample changer 75, sample changer 93 or sample changer 153) is disposed atop cylinder 115 which in turn is atop magnet chamber 113. Insertion tube 39 (or insertion tube 91, or insertion tube 107) is inserted into magnet chamber 113 via cylinder 115. Pneumatic lines 63 and 65 for control of drive 17 (or the corresponding drives of sample changer 75 or sample changer 93) are connected to magnet chamber 113 for provision of compressed air therefrom as described above, preferably.

Some of the many advantages of the present invention should now be readily apparent. For example, novel apparatus and method have been provided for repeated exchanging of similarly configured objects at a predetermined location. This apparatus and method can be used for sequentially inserting and removing solid samples to and from a device for testing such samples. In particular, a sample changer has been shown which can be used with an NMR spectrometer or other testing device which treats rotors or other holders for solid samples as if they were robust, not fragile devices. Utilizing the apparatus and method of the present invention, it is possible to provide automatic feed and ejection of samples to and from a testing device, thereby permitting unattended automatic operation of that testing device for extended periods of time. The apparatus and method of the present invention provides rapid, easy, automatic changing of samples to and from a device that tests such samples.

Obviously, many modifications and variations of the present invention are possible in light of the above teachings. It is, therefore, to be understood that the foregoing embodiments are presented by way of example only and that, within the scope of the appended claims and equivalents thereto, the invention may be practiced otherwise than as specifically described.

What is claimed is:

1. Apparatus for sequentially loading a plurality of solid sample rotors, one at a time, into an NMR spectrometer magnet chamber, said chamber having means for ejecting said rotor with an ejection velocity from said chamber, said apparatus comprising:
    a magazine for holding a plurality of rotors for loading into said magnet chamber;
    a spent rotor receptacle for receiving rotors ejected from said magnet chamber;
    a branched feed tube having a base leg connected to said magnet chamber, a first branch leg connected to said magazine and to said base leg, and a second branch leg connected to said spent rotor receptacle and to said base leg;
    means for transferring one of said plurality of rotors from said magazine to said first branch leg whereby said one rotor drops through said first branch leg and said base leg into said chamber, said one rotor subsequently being ejected through said base leg and said second branch leg; and
    means located in said second branch leg for reducing an ejection velocity of an ejected rotor so that said ejected rotor is not damaged by landing in said spent rotor receptacle.

2. Apparatus as recited in claim 1 wherein said magazine comprises a ramp having upper and lower ends, said ramp being connected at its lower end to said means for transferring.

3. Apparatus as recited in claim 2 wherein:
    said ramp is at least partially walled to prevent loss of the rotors therefrom; and
    said magazine further comprises a spring for urging the plurality of rotors down said ramp towards said means for transferring.

4. Apparatus as recited in claim 1 wherein said spent rotor receptacle comprises a funnel having a wider end connected to said second branch leg and a narrower end connected to a container.

5. Apparatus as recited in claim 1 wherein:
    said base leg and at least part of said second branch leg are coaxially aligned for smooth movement of a rotor therethrough; and
    said first branch leg is angled away from its connection to said base leg so as to freely permit passage of a rotor from said magazine through said first branch leg to said magnet chamber while disfavoring any movement of a rotor from said magnet chamber through said, base leg to said first branch leg.

6. Apparatus as recited in claim 1 wherein said means for transferring comprises:
    a first member, provided with an indentation; and
    a second member having a space therein configured to receive said first member therein, wherein said first member is slidably and rotatably disposed in said second member, and wherein said second member is connected to said magazine at a first location, and wherein said second member is at a second location connected to said first branch leg, and wherein said magazine and said first branch leg thereby each communicate with said space, and wherein said indentation can communicate with no more than one of said magazine and said first branch leg at any one time dependent upon the relative position of said first member within said second member.

7. Apparatus as recited in claim 6 wherein said magazine comprises a ramp having an upper end and a lower end, said ramp being connected at its lower end to said second member to communicate with said space of said second member.

8. Apparatus as recited in claim 1 wherein said means for reducing comprises a curve formed in said second branch leg between said spent rotor receptacle and said base leg.

9. Apparatus for sequentially loading a plurality of solid sample rotors, one at a time, into an NMR spectrometer magnet chamber, said chamber having means for ejecting said rotor with an ejection velocity from said chamber, said apparatus comprising:

a ramp for holding a plurality of rotors for loading into said magnet chamber, said ramp having upper and lower ends, said ramp being at least partially walled to prevent loss of the rotors therefrom and being provided with a spring for urging the plurality of rotors down said ramp;

a spent rotor receptacle for receiving rotors ejected from said magnet chamber;

a branched feed tube having a base leg connected to said magnet chamber, a first branch leg connected to said ramp and to said base leg, and a second branch leg connected to said spent rotor receptacle and to said base leg, wherein said base leg and at least part of said second branch leg are coaxially aligned for smooth movement of a rotor therethrough, and said first branch leg is angled away from its connection to said base leg so as to freely permit passage of a rotor from said ramp through said first branch leg to said magnet chamber while disfavoring any movement of a rotor from said magnet chamber through said base leg to said first branch leg;

means for transferring one of said plurality of rotors from said ramp to said first branch leg whereby said one rotor drops through said first branch leg and said base leg into said chamber, said one rotor subsequently being ejected through said base leg and said second branch leg, wherein said means for transferring comprises a first member provided with an indentation and a second member having a space therein configured to receive said first member therein, said first member being slidably and rotatably disposed in said second member, wherein said second member is connected at a first location to said lower end of said ramp, and wherein said second member is at a second location connected to said first branch leg, and wherein said ramp and said first branch leg thereby each communicate with said space, and wherein said indentation can communicate with no more than one of said ramp and said first branch leg at any one time dependent upon the relative position of said indentation within said second member; and a curve formed in said second branch leg between said spent rotor receptacle and said base leg.

* * * * *